(12) United States Patent
Laakso et al.

(10) Patent No.: US 6,960,456 B1
(45) Date of Patent: Nov. 1, 2005

(54) METHOD FOR PREPARING CONJUGATED LINOLEIC ACID

(75) Inventors: Simo Laakso, Turku (FI); Auli Rainio, Espoo (FI); Marjatta Vahvaselka, Helsinki (FI); Annika Mäyrä-Mäkinen, Helsinki (FI); Soile Tynkkynen, Helsinki (FI); Tarja Suomalainen, Helsinki (FI)

(73) Assignee: Valio Ltd., Helsinki (FI)

( * ) Notice: Subject to any disclaimer, the term of this patent is extended or adjusted under 35 U.S.C. 154(b) by 373 days.

(21) Appl. No.: 10/130,426

(22) PCT Filed: Nov. 16, 2000

(86) PCT No.: PCT/FI00/01004

§ 371 (c)(1),
(2), (4) Date: Jul. 9, 2002

(87) PCT Pub. No.: WO01/36653

PCT Pub. Date: May 25, 2001

(30)    Foreign Application Priority Data

Nov. 19, 1999    (FI) .............................................. 19992477

(51) Int. Cl.$^7$ ................................................. C12P 7/64
(52) U.S. Cl. ....................................................... 435/134
(58) Field of Search ......................................... 435/134

(56)              References Cited

U.S. PATENT DOCUMENTS 5,856,149 A      1/1999  Pariza et al.
6,706,501 B1 *   3/2004  Rosson et al. .............. 435/134

FOREIGN PATENT DOCUMENTS

WO        99/32604      1/1999
WO        99/29886      6/1999

OTHER PUBLICATIONS

Park et al, "Changes in Body Composition in Mice During Feeding and Withdrawal of Conjugated Linoleic Acid", Lipids, vol. 34, No. 3 (1999), pp. 243–248.
Lee et al, "Conjugated Linoleic Acid and Atherosclerosis in Rabbits", Atherosclerosis 108 (1994) 19–25.
Pariza et al, "Mutagens and Modulator of Mutagenesis in Fried Ground Beef", Cancer Research (Suppl.) 43, 2444s–2446s, May, 1983.
Pariza et al, "A Beef–Derived Mutagenesis Modulator Inhibits Initiation of Mouse . . . ", Carcinogenesis, vol. 6, No. 4, pp. 591–593, 1985.
Clement et al, "Mammary Cancer Prevention by Conjugated Dienoic Derivative of Linoleic Acid", Cancer Research, 51, 6118–6124, Nov. 15, 1991.
Suutari et al, "Temperature Adaptation in Yeasts: the Role of Fatty Acids", Journal of General Microbiology (1990), 136, 1469–1474.
Verhulst et al, "Isomerization of polyunsaturated long chain fatty acids by propionibacteria", 1987:436348, abstract.
Jiang et al, "Production of conjugated linoleic acid by dairy starter cultures", 1998:575415, abstract.

* cited by examiner

*Primary Examiner*—Herbert J Lilling
(74) *Attorney, Agent, or Firm*—Nixon & Vanderhye P.C.

(57)              ABSTRACT

The invention relates to a method for preparing conjugated linoleic acid and particularly its cis-9,trans-11 isomer from linoleic acid by fermentation. The invention also relates to products prepared by the method.

18 Claims, 1 Drawing Sheet

METHOD FOR PREPARING CONJUGATED LINOLEIC ACID

Figure 1:
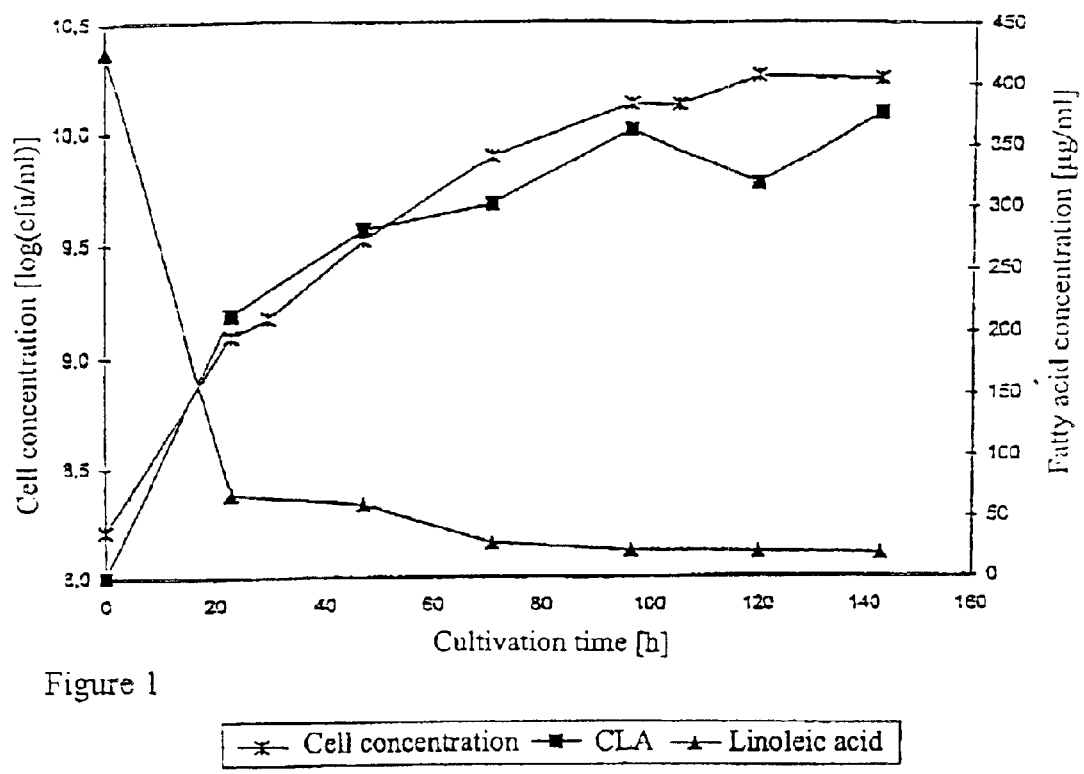

This application is in US national phase of international application PCT/FI00/01004 filed 16 Nov. 2000, which designated the US.

FIELD OF THE INVENTION

The invention relates to a method for preparing conjugated linoleic acid. In particular, a method is described for preparing the conjugated linoleic acid and particularly its cis-9,trans-11 isomer from linoleic acid by fermentation.

BACKGROUND OF THE INVENTION

CLA is a generic term for various isomers of conjugated linoleic acid, of which only two isomers (the cis-9,trans-11 isomer, i.e. bovinic acid, and a trans-10,cis-12 isomer) are found to be biologically active. Synthetically produced, commercial CLA preparations generally contain all different isomers of CLA and only 40% of the c9,t11 isomer, whereas milk contains 80% of the c9,t11–18:2 isomer.

Several studies have reported that animal fats contain a fatty acid that, among other things, inhibits cancer in test animals, affects growth factors and may control the amount of fatty tissue in an organism. While studying hamburger beefs, Michael Pariza found that they contained a fatty acid that was assayed to be conjugated linoleic acid (CLA). It was found in animal tests that in the group of those fed with CLA-containing diet the number of mammary, stomach and colon cancer incidences was reduced as compared with the reference group (Pariza, M. W., Loretz, L. J., Storkson, J. M. and Holland, N. C., Mutagens and modulator of mutagenesis in fried ground beef, *Cancer Res.* (Suppl.), 1983, 43:2444s–2446s and Pariza, M. W. and Hargraves, W. A., A beef-derived mutagenesis modulator inhibits initiation of mouse epidermal tumors by 7,12-dimethylbenzanthracene, *Carcinogenesis,* 1985, 6:591–593). Also in tissue cultures of human cells, CLA has been capable of inhibiting development of cancer cells. The mechanism how it acts is still unknown, but CLA has been found to have an effect on various stages of tumorigenesis, many growth factors and also possibly on the metabolism of carcinogenic substances in the liver. It has also been suggested that CLA would act as an antioxidant (Ip, C., Chin, S. F., Scimeca, J. A. and Pariza, M. W., Mammary cancer prevention by conjugated dienoic derivatives of linoleic acid, *Cancer Res.,* 1991, 51:6118–124), whereby the compound would protect cell membranes from the adverse effect of free radicals. The cholesterol-lowering effect of the compound has also been studied and found that the compound does not reduce the amount of the good high density lipoprotein (HDL) as the cholesterol-lowering drugs do (Lee, K. N., Kritchevsky, D. And Pariza, M. W., Conjugated linoleic acid and atherosclerosis in rabbits, *Atherosclerosis,* 1994, 108:19–25). CLA may also be beneficial to slimmers, because the compound has been found to split fatty tissues (Park et al., Changes in Body Composition in Mice during Feeding and Withdrawal of Conjugated Linoleic Acid, *Lipids,* 1999, 34:243–248).

Unconjugated linoleic acid, in turn, has been reported to have adverse effects, e.g. a stimulating effect on breast cancer. The antimicrobial effect of unconjugated linoleic acid is also commonly known.

CLA can be produced chemically or by enzymatic isomerization. Natural CLA is formed e.g. in the rumen of ruminant animals from polyunsaturated fatty acids as a result of biological activity of the bacterium *Butyrivibrio fibrisolvens* and is secreted therefrom both into milk and meat, which are found to be the best sources of CLA.

It has been found that the amount of CLA received from food has considerably decreased during the past decade. It is calculated in dietary analyses that in the 1970s an average diet contained about 0.45 g of CLA daily. As the use of milk and milk products has decreased, an average daily intake is currently 0.25 g of CLA. To increase natural CLA in food is highly essential in view of public health, because to double the CLA intake would reduce the risk of cancer, for instance, according to researches.

Several studies have reported on the importance of milk, in particular, of all foods as a source of CLA. For instance, according to a Finnish epidemiological survey (Knekt et al., oral statement) use of milk reduced the risk of breast cancer. Currently, CLA concentration in milk fat varies seasonally considerably (2.4 to 28.1 mg/g fat) depending on the quality of feeding.

Useful microbes in Intestinal tracts have been found to form CLA. Particularly, *Butyrivibrio fibrisolvens* bacterium occurring in the rumen and an isomerase enzyme thereof have been studied. However, this bacterium is so anaerobic that it is not possible to produce CLA therewith on an industrial scale, because the fully anaerobic conditions required by the strain are difficult and uneconomical to achieve (U.S. Pat. No. 5,856,149, Pariza et al.)

*Propionibacterium* acnes has also been found to produce CLA, but this pathogenic strain also produces a reductase enzyme which reduces the produced CLA further to other fatty acids (Verhulst et al., *System. Appl. Microbiol.,* 9:12–15 (1987).

It is also commonly known that some propionic acid bacteria are capable of converting linoleic acid to the conjugated cis-9,trans11 form thereof.

Moreover, it is commonly known that the conversion of free linoleic acid to CLA is more efficient than that of the fatty acid in the form of a triglyceride. However, the free linoleic acid has an inhibitory effect on the growth of propionic acid bacteria even in relatively low concentrations, which has so far prevented the production of the conjugated linoleic acid, and particularly the cis-9,trans-11 form thereof, on a large scale.

U.S. Pat. No. 5,856,149 (Pariza and Yang) discloses a method of producing a cis-9,trans-11 fatty acid by conversion of unconjugated unsaturated (double bonds at positions 9 and 12) fatty acid with a strain of *Lactobacillus reuterii,* preferably *L. reuterii* PYR8. The publication describes isolation of CLA-producing strains, and states that only four of the 45 isolated strains had the desired linoleate isomerase activity and they were thus able to produce CLA from the linoleic acid. The researchers observed that the amount of CLA produced was in direct proportion to the amount of cells, and assume that the linoleate isomerase is an accumulating enzyme that has no functional significance in cell growth. The publication does not state an inhibitory effect of the linoleic acid on bacterial growth, and consequently, no solution is set forth to solve this problem.

In the article Production of conjugated linoleic add by dairy starter cultures, *J. Appl. Microbiol,* 85 (1998), pp. 95–102, J. Jiang, L. Björck and R. Fonden set forth that propionic acid bacteria are able to convert linoleic acid to CLA. Jiang et al. studied the ability of 19 different starter bacteria to convert the linoleic acid added to a growth medium to CLA after having observed that ripened cheeses contained higher levels of CLA than other milk products. They studied the ability of 7 lactobacillus strains, 4 lactococcus strains, 2 streptococcus strains and 6 propionic acid bacteria to produce CLA from linoleic acid in MRS, milk and Na-lactate media. In addition, different linoleic acid concentrations were studied by adding linoleic acid to MRS broth in an aqueous solution of Tween 80 detergent. Only a few propionic acid bacteria of the studied bacteria were observed to have bioconversion activity, three out of six strains, i.e. *Propionibacterium freudenreichii* ssp. *freudenreichii* PFF and PFF6 and *P. freudenreichii* ssp. *shermanii* PFS exhibited activity. The highest yield 265 μg/ml of CLA from the original linoleic acid concentration of 750 μg/ml was achieved with the PFF6 strain. Of the produced CLA, 70 to 90% was biologically active c9,t11 isomer. None of the lactobacilli, lactococci or streptococci was found to produce CLA.

Thus, the best propionic acid bacterium, the PFF6 strain, was capable of converting only 35% of the added linoleic acid to CLA with the technique described by Jiang et al. The researchers observed that the CLA production of propionic acid bacteria correlates positively with their tolerance to free linoleic acid. Thus, this study also confirmed the commonly known fact that the linoleic acid has an antimicrobial effect which inhibits the growth of bacteria. The publication states that the effect of antimicrobial fatty acids can be reduced by using surfactants, such as a detergent, e.g. Tween 80, or proteins. Studies on these lines have not been conducted, however, and the publication does not describe possible, useful techniques.

WO 99/29886, by J. Jiang, L. Björck and R. Fonden, is partly based on the research results set forth in the above-mentioned article. The application relates to the use of specific bacteria, useful in foodstuff applications, to produce CLA in vitro. In addition to *Propionibacterium freudenreichii* ssp. *freudenreichii* and *P. freudenreichii* ssp. *shermanii,* suitable bacteria also include *Bifidobacterium breve*. According to the publication, fermentation can be performed in the presence of an emulsifier, as examples are given Tween 80 and lecithin. However, the use of an emulsifier is not described in the examples of this publication, either, and the best result obtained is reported to be the same as in the above publication: 246.4 μg/ml of biologically active c9,t11 isomer was obtained from the original linoleic acid concentration of 750 μg/ml by using the strain PFF6. The yield is thus less than 33%.

Consequently, there is still an obvious need to provide new methods for producing conjugated linoleic acid with improved yields. When there is a desire to utilize the largest possible amounts of free linoleic acid as the starting material of CLA, the essential thing is how the problems associated with the antimicrobial effect of the free linoleic acid can be minimized or avoided.

BRIEF DESCRIPTION OF THE INVENTION

The object of the present invention is to provide a new method for producing conjugated linoleic acid with a good yield.

The object of the present invention is also to provide new products which are manufactured by utilizing the method of the invention and which contain a large amount of CLA.

DETAILED DESCRIPTION OF THE INVENTION

The present invention is based on the idea that the inhibitory effect of free linoleic acid on the growth of bacteria is reduced by adding linoleic acid to a medium in a form that does not considerably inhibit the growth of bacteria but is available to them during the cultivation.

According to the invention, it has been found that when the linoleic acid is added to a reaction broth as a micellar mixture it has a considerably lower inhibitory effect on the growth of bacteria than the linoleic acid in any other form. By means of a suitably large detergent addition the linoleic acid is maintained micellar under cultivation conditions. This also reduces, for its part, the inhibitory effect of the linoleic acid on the growth of bacteria. The use of micellar linoleic acid and the stabilization of the micelles during the cultivation also enable a considerably improved yield of CLA.

By using micellized linoleic acid as the starting material for fermentation and by selecting an appropriate linoleic-acid-to-detergent proportion it is possible to achieve over 90% conversion of the linoleic acid to CLA and over 97% of the formed CLA is secreted to the medium. According to the present invention, a method is thus developed to prepare large amounts of linoleic acid to a form which enables the bacteria to efficiently convert the linoleic acid to CLA, in particular to c9,t11 isomer, without the reaction suffering from the inhibitory effect of the linoleic acid on the growth.

The invention thus relates to a method for preparing CLA from linoleic acid with microorganisms, the method being characterized in that the linoleic acid used as starting material is added to the reaction broth in the form of micelles.

The micelles contain free linoleic acid and surfactant in an appropriate proportion.

The invention further relates to products manufactured by the method of the invention and their use as such or in the manufacture of functional foods and health-promoting substances.

Micellization can be carried out in a simple manner by mixing linoleic acid with a micelle-forming detergent in an appropriate proportion under alkaline conditions. The preparation does not require special conditions nor special equipment. It is simple, inexpensive and easy to carry out also on a large scale.

Free linoleic acid is used for micellization according to the invention. Free linoleic acid is commercially available. Alternatively, it is also possible to prepare free linoleic acid from vegetable oils, e.g. safflower oil, maize oil or sunflower oil, by hydrolyzing the fatty acids free using saponification by methods known per se (cf. e.g. Christie, W. W., Gas Chromatography and Lipids—a Practical Guide, 2. edition, 1989, The Oily Press, Ayr, Scotland).

This is often an economical alternative considering that the pure, free linoleic acid is very expensive. And, synthetically prepared linoleic acid is not always suitable for use in foodstuffs due to chemical residues.

Safflower oil is an advantageous source of linoleic acid. It contains up to 78% of linoleic acid and the free fatty acid preparation made therefrom is up to hundred times more economical than the commercially available free linoleic acid.

From the viewpoint of the invention, selection of the surfactant is not a critical parameter, for instance polyoxyethylene sorbitane esters (Tween preparations)(several manufacturers, e.g. Fluka and Sigma) and PEG 20 sorbitane oleate Kotilen-0/1 VL (by Dr. W. Kolb AG) widely used in the field of microbiology are well suited for this purpose. Several other surfactants are also applicable.

Conversion of the micellized linoleic acid, prepared in the above-described manner, to CLA can be carried out effectively by fermentation. In fermentation, it is possible to use any bacterium that is capable of converting linoleic acid to CLA, such as the bacteria appearing in the above background art description. However, fermentation is advantageously performed with food grade bacteria, in particular, propionic acid bacteria. Suitable strains include, for instance, those of *Propionibacterium freudenreichii* species and in particular the strains belonging to the subspecies *P. freudenreichii* ssp. *freudenreichii* and *P. freudenreichii* ssp. *shermanii*.

The micellar linoleic acid is stabilized by adding surfactant, i.e. detergent, to the medium in an amount that eliminates the effect of the medium. Above-mentioned substances, such as Tween and Kotilen, can be used as surfactants. The advantageous surfactant concentration depends on the amount of added micellar linoleic acid and on the medium used. The detergent is generally used in an amount of 0.5 to 1.5%, preferably 1%. Micellized linoleic acid is thus added to the fermentation broth as starting material for CLA.

The novel technique according to the invention allows to add line leic acid up to at least 1,000 µg/ml medium to the fermentation broth without that the growth of bacteria considerably changes or the conversion efficiency decreases. Thus, bioconversion is considerably better with this technique than with known techniques, i.e. at least 80% of the linoleic acid converts to CLA, and of that CLA amount at least 75% is the biologically most active isomer.

Fermentation is carried out in a manner known per se. Media and conditions are selected to satisfy the requirements of the strain to be used in order to provide an optimum yield of CLA. After making the present invention available to the public, the selection of suitable fermentation parameters will be obvious to the person skilled in the art.

Using the micellized linoleic acid, it is thus possible to produce CLA in connection with bacterial growth by eliminating the growth-inhibiting effect of the linoleic acid. CIA can also be produced simultaneously with cell production intended for other purposes. One6: special feature of the method according to the invention is that CLA can also be produced after cell cultivation or separately therefrom, using dormant, i.e. non-growing, cells, whereby CLA can be produced both in a nutrient medium and in a buffer solution. No separate addition of detergent is needed in the buffer solution to stabilize the linoleic acid detergent micelles. If desired, CLA formation can also be combined to take place directly in the (food) product to be manufactured in a manufacturing process utilizing the bacterium concerned.

The CLA formed in the fermentation and secreted outside the cells can be isolated from the fermentation broth by background art techniques, and if desired, modified into a highly purified CLA product by methods known per se. Alternatively, the fermentation broth containing CLA and bacterial cells can be used as such, or the CLA can be concentrated or dried with the bacterial cells.

The obtained CLA-containing product can be used as such as a health-promoting substance. The product can also be used in the manufacture of functional foods and the like.

In the present document, the term food is used in a broad sense covering all edible products which can be in solid, jellied or liquid form, and covering both ready-to-eat products and products to which the product of the invention is added in connection with consumption, as an additive or to be a constituent component of the product. For instance, foods can be products of dairy industry, meat processing industry, food processing industry, beverage industry, baking industry and confectionery industry. Typical products include milk products, such as yogurt, curdled milk, curd cheese, sour milk, buttermilk and other fermented milk beverages, unripened cheeses and ripened cheeses, snack fillings, etc. Beverages, such as whey beverages, fruit beverages and beers, constitute another important group.

Lyophilized preparations, such as CLA-containing capsules and powders of propionic acid bacterium, and fermented milk products whose CLA-content is raised by the activity of the propionic acid bacterium, are regarded as preferred embodiments.

In the following, the invention will be described in greater detail by means of examples. These examples are only intended to illustrate the invention, not to restrict its scope in any way.

REFERENCE EXAMPLE 1

Effect of Micellization on Bacterial Growth and Production of CLA

To prove the effect of the method according to the invention, a comparative test was carried out, which studied the growth and production of CLA of propionic acid bacteria in a medium containing free linoleic acid, free linoleic acid and detergent, and linoleic acid micellized according to Example 1 and detergent. As controls were used the same medium without addition (positive growth control) and a medium to which only detergent was added.

For the test, the propionic acid bacterium strains *Propionibacterium freudenreichii* ssp. *shermanii* JS (PJS), DSM 7067, and *P. freudenreichii* ssp. *freudenreichii* 131 (P131) were first cultivated in MRS broths with 1) no addition
2) 600 µg/ml linoleic acid
3) addition of 600 µg/ml linoleic acid from a stock solution containing 5 mg/ml linoleic acid and 1% of Tween 80 preparation in an aqueous solution (final content of Tween 0.2%)
4) addition of 0.9% of Kotilen and 600 µg/ml linoleic acid micellized according to Example 1
5) addition of 0.9% of Kotilen only (not linoleic acid)

The PJS strain deposited on May 13, 1992 under Accession No. DSM 7067 at the DSM-Deutshe Sammlung Von Mikroorganismen Und Zellkulturen GmbH, Mascheroder Weg 1 B, D-3300 Braunschweig.

The PJS strain was also cultivated in a whey-based medium which contained 5% of whey permeate (Valio Oy), 2% of casein hydrolysate (Valio Oy) and 1% of yeast extract (LabM), with above additions 1 to 5.

Each bacterium strain was cultivated in the culture medium twice at 30° C. for 72 h, whereafter each test broth was inoculated with 1% of fresh culture. The test cultures were monitored at 30° C. for 4 days by determining the cell density of the culture as turbidity with a Klett meter. At the end of cultivation (96 h), the amount of formed CLA was determined by gas chromatography, the c9,t11 isomer separately and the other isomers together.

Assays of fatty acids were carried out, with some modifications, as M.Suutari, K. Liukkonen and S. Laakso set forth in the article Temperature adaptation in yeasts: the role of fatty acids, *J. Gen. Microbiol.*, 136 (1990) 1469–1474. Samples of the medium were taken for the assays and the cells were separated by centrifugation (5,000 g, for 15 min). The supernatant was filtered on a 0.2 µm filtre and samples of 0.2 to 0.5 ml were taken. The cell mass was washed with tap water. The supernatant samples and the washed cells were freeze-dried.

To the freeze-dried samples was added 1 ml of saponifying reagent which was 3.7 M NaOH solution in 49% methanol. The samples were treated with nitrogen, mixed and incubated-in closed tubes at 100° C. in a water bath for 30 min mixing once during that time. The samples were cooled to room temperature and thereto was added 4 ml of methylation reagent which was 3,3 M HCl solution in 48% methanol. The samples were treated with nitrogen, mixed and the sample tubes were incubated in a water bath at 80° C. for 10 min, whereafter they were cooled. Methyl esters of the fatty acids were extracted by adding 1.5 ml of hexane/methyltertbutyl ether solution (1:1) to the samples and by shaking the tubes vigorously for 10 min. The lower aqueous phase was removed with a Pasteur pipette. The organic layer was washed by adding 3 ml of 0.3 M NaOH solution to the samples and by shaking the tubes vigorously for 5 min. The samples were centrifuged (5,000 g; for 20 min) and the organic sample layer was recovered with a Pasteur pipette. The samples were dried with sodium sulphate and treated with nitrogen.

The methyl esters of the fatty acids were assayed with a gas chromatograph (Hewlett Packard 5890 series 11, Pennsylvania, USA) to which was connected a flame ionization detector (FID) and an automatic sampling device (Hewlett Packard 7673A). A capillary column (HP-FFAP, 25 m×0.2 m×0.3 $\mu$m) was used in the assays. The samples were injected with split injection (split ratio being 1:20; septum wash rate being 1 to 2 ml/min). Inlet pressure of the column was 150 kPa and the flow rate of the carrier gas (helium) into the column was about 1 ml/min. The flow rate of the make up gas (air) was 30 ml/min and the flow rate of hydrogen into the detector was 40 ml/min. Injection temperature and detector temperature were 250° C. The oven temperature was 70 to 200° C. The temperature rose at a rate of 25 degrees Celsius per minute. The results were processed and outputted with HP Chemstation software connected to the gas chromatograph.

The fatty acids of the samples were identified by comparing their retention times with those of known fatty acid standards. A preparation by Sigma was used for identifying conjugated linoleic acid, the preparation being a mixture of cis- and trans-9,11 and -10,12 isomers of CLA. To quantify the fatty acids, C19:0 fatty acid methyl ester (nonadecanoic acid methyl ester, Sigma) was used as an internal standard.

The growth results of the bacteria are presented in Table 1.1.

TABLE 1.1

Growth of PJS and P131 strains in MRS medium containing linoleic acid (LA)

| | 0 h | 24 h | 48 h | 72 h | 96 h |
|---|---|---|---|---|---|
| PJS | | | | | |
| 1) control | 2 | 38 | 180 | 325 | 415 |
| 2) LA | 78 | 84 | 96 | 106 | 110 |
| 3) LA + detergent | 40 | 49 | 68 | 94 | 120 |
| 4) LA (micelle) + detergent | 11 | 36 | 125 | 252 | 370 |
| 5) detergent | 1 | 35 | 185 | 340 | 430 |
| P131 | | | | | |
| 1) control | 8 | 37 | 122 | 270 | 425 |
| 2) LA | 80 | 90 | 97 | 107 | 115 |
| 3) LA + detergent | 55 | 60 | 74 | 95 | 114 |
| 4) LA (micelle) + detergent | 1 | 20 | 71 | 160 | 270 |
| 5) detergent | 0 | 22 | 104 | 244 | 410 |

It appears from the results that the linoleic acid having a concentration of 600 $\mu$g/ml as such or added via stock solution having 1% of Tween in aqueous solution inhibited the growth of both strains as compared with the control. By using a corresponding amount of linoleic acid micellized according to the invention the inhibitory effect of the linoleic acid on growth was reduced and the strain grew almost in the same manner as the control.

The amount of CLA formed by PJS and P131 strains in MRS-based broths is presented in Table 1.2 and a corresponding result with PJS strain in a whey-based medium is presented in Table 1.3.

TABLE 1.2

Formation of CLA by PJS and P131 strains in MRS medium containing linoleic acid (LA)

| | Total CLA $\mu$g/ml culture | CLA (c9,t11) $\mu$g/ml culture | CLA yield % | Proportion of c9, t11 isomer of total CLA (%) |
|---|---|---|---|---|
| PJS | | | | |
| 1) control | 39 | 9 | — | 24 |
| 2) LA | 195 | 135 | 32 | 69 |
| 3) LA + detergent 0.2% | 279 | 227 | 47 | 81 |
| 4) LA (in micelles) + detergent 0.9% | 680 | 490 | 100 | 73 |
| 5) detergent 0.9% | 247 | 64 | — | 26 |
| P131 | | | | |
| 1) control | 41 | 11 | — | 26 |
| 2) LA | 66 | 16 | 11 | 25 |
| 3) LA + detergent 0.2% | 78 | 26 | 13 | 34 |
| 4) LH (in micelles) + detergent 0.9% | 308 | 134 | 51 | 44 |
| 5) detergent 0.9 % | 232 | 63 | — | 27 |

TABLE 1.3

Formation of CLA by PJS strain in whey permeate medium containing linoleic acid (LA)

| PJS | Total CLA $\mu$g/ml culture | CLA (c9,t11) $\mu$g/ml culture | CLA yield % | Proportion of c9,t11 isomer of total CLA (%) |
|---|---|---|---|---|
| 1) control | 16 | — | — | — |
| 2) LA | 13 | — | — | — |
| 3) LA + detergent 0.2% | 53 | 13 | 2 | 25 |
| 4) LA (in micelles) + detergent 0.9% | 440 | 420 | 13 | 96 |

It appears from the results that micellization according to the invention enables a nearly 100% conversion of linoleic acid to CLA, of which up to over 75% is advantageous c9,t11 CLA isomer. If the linoleic acid is added as such, only 32% is converted to CLA, and if the linoleic acid is added in a 1% detergent solution, only 47% is converted to CLA. Thus, a considerably better result is achieved with the micellization according to the invention as regards both the minimization of the inhibitory effect of the linoleic acid on bacterial growth and the maximization of CLA production from the linoleic acid.

Example 1

Preparation of Linoleic Acid into Micelles

To produce a micellar stock solution, 300 mg of linoleic acid (cis-9,trans-12 octadecadienoic acid, L-1376, Sigma) was weighed into a test tube, 10 ml of oxygen-free distilled water containing 0.36 ml of sorbitane oleate detergent (Kotilen 0/1 or Tween 80) was added and gently mixed. To the mixture was added 2 N sodium hydroxide solution dropwise such that the mixture barely clarified (about 0.5 to 0.6 ml). The solution was transferred into a 50 ml volumetric flask and the flask was filled to mark with oxygen-free distilled water, whereby a micellar stock solution containing 6 mg/ml linoleic acid was obtained. The solution was divided into suitable batches, air was removed by means of nitrogen gas and the batches were stored frozen.

The stock solution of micelles can also be prepared more concentrated or more diluted than what is described above. It is essential that the proportion between the amounts of the free linoleic acid and the sorbitane oleate detergent remains the same as above.

Example 2

Effect of Linoleic Acid and Detergent on Bacterial Growth and Production of CLA The effect of the proportion of linoleic acid to detergent was examined by cultivating propionic acid bacteria in a whey-based growth broth and MRS broth (LabM) in cultures of 150 ml. The whey-based broth contained 2% of whey permeate (Valio Oy), 0.5% of trypton (LabM) and 1% of yeast extract (LabM). The linoleic acid was added to the medium as the above-described stock solution in the form of micelles such that the concentration of free linoleic acid in the medium was 600 μmg/ml. A desired amount of sorbitane oleate detergent (Kotilen 0/1 or Tween 80) was added to the medium separately. The pH of the medium was adjusted to 6.3. the propionic acid bacterium strain *P. freudenreichii* ssp. *shermanii* JS was used in the cultures as a 2% (v/v) inoculum that had been cultivated in a whey-based broth. Cultivation took place at a temperature of 30° C. Cell growth was monitored for 96 hours by measuring the turbidity of the medium with a Klett-Summerson colorimeter (filtre No. 66). CLA and linoleic acid were assayed gas chromatographically.

The results are presented in Table 2. Production of CLA refers herein and in CLA results of examples 3 to 4 to the CLA formed by PJS microbial cells, calculated by subtracting from the total CLA concentrations the amount of CLA originating in the medium from the detergent. The CLA yield is calculated as follows: g of formed CLA/g of LA initially.

TABLE 2

Effect of detergent concentrations of whey permeate broth and MRS broth [x)] on PJS growth and production of CLA

| Detergent addition to whey permeate broth | Δ Klett value | CLA yield (%) |
|---|---|---|
| LA (control) | 34 | <1 |
| 0.9% Kotilen (control) | 365 | <1 |
| LA + 0.2% Kotilen | 77 | 33 |
| LA + 0.9% Kotilen | 306 | 65 |
| LA + 1.2% Kotilen | 309 | 67 |
| Detergent addition | | |

TABLE 2-continued

Effect of detergent concentrations of whey permeate broth and MRS broth [x)] on PJS growth and production of CLA

| Detergent addition to whey permeate broth | Δ Klett value | CLA yield (%) |
|---|---|---|
| to MRS broth | | |
| LA + 0.1% Tween 80 | 56 | 51 |
| LA + 0.8% Tween 80 | 301 | 83 |

[x)] MRS broth contains 0.1% of Tween 80, consequently by 0.1% addition the final concentration rises to about 0.2%.

Linoleic acid can be added in large amounts in micellar form to the growth medium of the PJS strain without that inhibiting completely the cell growth. It appears from the results in Table 2 that the detergent addition further allows to reduce the inhibitory effect of linoleic acid. When the proportion of the linoleic acid to the detergent is appropriate in the medium, the amount of linoleic acid can be raised in the medium such that its conversion to CLA in connection with cellular growth occurs as efficiently as in small linoleic acid concentrations. Industrially significant amounts of the desired cis-9,trans-11 isomer of CLA are thus achieved. With the linoleic acid concentration of 600 μg/ml a detergent content of 0.9 to 1% was optimal in this test, but larger amounts can also be used.

Example 3

Production of CLA in pH-Adjusted Fermentation

The most efficient way to cultivate propionic acid bacteria on an industrial scale is to do it in a fermentor where the pH of the medium can be maintained optimal for cellular growth. A production process of conjugated linoleic acid by means of growing PJS cells was examined in fermentor cultures the solution volume being 2 liters. The whey permeate broth of Example 2 was used as growth medium. The growth broth contained micellized linoleic acid 400, 600, 1000 or 1400 μg/ml and Kotilen detergent 0.6, 0.9 or 1.5%, respectively. During the cultivation, the pH of the growth medium was maintained at 6.3 with linoleic acid concentrations of 400, 600 and 1000 μg/ml and at 6.5 with linoleic acid concentration of 1400 μg/ml by means of an automatic addition of ammonium solution. The cultivation temperature was 30° C. and the mixing rate was 100 rpm. The concentration of viable propionic acid bacteria cells was determined in buffered sodium lactate agar and the agar dishes were incubated at 30° C. anaerobically for 5 to 7 days.

FIG. 1 shows CLA formation from linoleic acid when 400 μg/ml of linoleic acid and 0.6% of sorbitane oleate detergent were added to the medium. The conversion of linoleic acid to CLA clearly occurs simultaneously with the growth of PJS cells.

Table 3 compares the CLA production process in a fermentor, with the linoleic acid content in the medium of 400, 600 and 1000 μg/ml, after 94 hour cultivation, and that of 1400 μg/ml, after 108 and 132 hour cultivation.

TABLE 3

Production of CLA in pH-adjusted culturing of PJS cells

|  | LA 400 µg/ml deterg. 0.6% 94 h | LA 600 µg/ml deterg. 0.9% 94 h | LA 1000 µg/ml deterg. 1.5% 94 h | LA 1400 µg/ml deterg. 1.5% 108 h | LA 1400 µg/ml deterg. 1.5% 132 h |
|---|---|---|---|---|---|
| cell concentration (cfu/ml) | $1.3 \times 10^{10}$ | $1.2 \times 10^{10}$ | $1.4 \times 10^{10}$ | $2.4 \times 10^{9}$ | $1.3 \times 10^{10}$ |
| CLA concentration (µg/ml) | 515 | 886 | 1270 | 1490 | 1650 |
| CLA yield (%) | 84 | 77 | 63 | 79 | 91 |
| proportion of extracellular CLA (%) | 98 | 99 | 98 | 99 | 99 |
| proportion of cis-9,trans-11 (%) | 75 | 83 | 73 | 95 | 94 |
| proportion of cis-9,trans-11 (%) * | — | — | — | 81 | 82 |
| consumption of linoleic acid (%) | 93 | 94 | 92 | 90 | 92 |

* contains also CLA originating from Kotilen.

Example 4

Production of CLA After Cell Growth Phase

The ability of propionic acid bacteria to produce CLA after the cell growth phase was examined by repeating the fermentation of Example 3 with the difference that the linoleic acid and the sorbitane oleate detergent in the micellar solution were added to the broth only at the end of the fast cell growth phase of PJS cells, after 51 hours from the beginning of cultivation. The linoleic acid concentration in the medium was 600 µg/ml and that of the detergent 0.9%. Cell concentration at the moment of addition was $1.8 \times 10^{10}$ cfu/ml. Thereafter the cell growth stopped for about three hours and then continued very slowly.

The conversion from linoleic acid to CLA produced by the cells took place very quickly: in three hours the CLA yield was 45% and in six hours 58%. An advantage of this method is a shorter total duration of fermentation (about 60 hours) as compared with corresponding cultivation where the linoleic acid and the detergent were present in the growth medium since the beginning (about 100 hours).

Example 5

Use of Non-Growing Bacterial Cells for CLA Production in Buffer Solution

PJS cells were cultivated in a whey-based growth broth for 3 days at 30° C., the cells were subjected to centrifugation and washed with a 0.1 M sodium phosphate buffer (pH 6.0). 2.0 g of wet cellular mass was added to 50 ml of 0.1 M sodium phosphate buffer (pH 7.8), whereby the cell concentration in the buffer became about $3 \times 10^{10}$ cfu/ml. Linoleic acid micellized according to Example 1 was added such that the linoleic acid concentration in the buffer solution became 600 µg/ml. The solution was incubated at a temperature of 6° C. or 30° C. for 21 hours. CLA was assayed by the GC method and by measuring with a spectrophotometer at a wavelength of 235 nm.

The results are presented in Table 4. CLA formation in the buffer solution by means of non-growing PJS cells occurred at either temperature studied, it was most efficient at 30° C. CLA production in the nutrient solution requires added detergent for maintaining the linoleic acid in the micellar form. An advantageous detergent concentration depends on the starting material concentration of the solution. In the buffer solution, in turn, no separate detergent addition to the reaction broth is required, it can even be clearly harmful.

TABLE 4

CLA yield (g of formed CLA/ g of LA with non-growing PJS cells in phosphate buffer, pH 7.8)

|  | CLA yield (%) | |
|---|---|---|
| Reaction time (h) | 6° C. | 30° C. |
| 3 | 3 | 20 |
| 5 | 5 | 29 |
| 21 | 20 | 63 |

Example 6

Production of CLA from Safflower Oil a) Saponification of Safflower Oil

Fatty acids are released from safflower oil by saponification under mild conditions with an antioxidant, whereby oxidation of linoleic acid is prevented. For saponification, potassium or sodium hydroxide, ethanol, water and ascorbic acid are used for instance in the following proportions: safflower oil 10 g, saturated KOH water solution 5 ml, ethanol 50 ml, water 10 ml (the amount can also be lower) and ascorbic acid 1 g. The mixture is treated with nitrogen and the cap is closed tightly. The mixture is saponified overnight by magnetic mixing. Unsaponified moiety is extracted from the solution with e.g. 30 ml of hexane. To prevent emulsification, water can also be added to the mixture. Thereafter the solution is acidified (pH 2 to 3) with concentrated hydrochloric acid. The fatty acids are extracted from the solution e.g. twice with 40 ml of hexane. The hexane is evaporated in a rotating evaporator, the fat is transferred to a bottle having a tight screw cap and is treated with nitrogen for a few minutes. Thereafter the fat mixture is ready and it is stored in a freezer to prevent from becoming oxidized.

b) Formation of Micelles

Fatty acid micelles are prepared in accordance with the present invention from a mixture of free fatty acids prepared from safflower oil by means of Kotilen, water and sodium hydroxide, for instance in the following proportions: safflower oil preparation 700 mg, water 30 ml, Kotilen 0.75 ml, 2 N sodium hydroxide solution 1.5 ml. Prior to mixing, Kotilen and water can be heated to about 40° C. Kotilen is mixed with water treated with nitrogen. Safflower oil preparation is added to the mixture by mixing well. Finally, sodium hydroxide solution is added dropwise, whereby the mixture clarifies.

c) Production of CLA

CLA can be produced from the fat solution with a bacterium for instance in the following manner: To a growth medium, which contains e.g. 2% whey permeate, 0.5% casein hydrolysate, 0.5% yeast extract and 0.9% Kotilen, is added a solution containing linoleic acid and a 2% inoculum of *Propionibacterium freudenreichii* ssp. *shermanii* JS culture that has grown for three days. The CLA yield (%) produced with the bacterium at a temperature of 30° C. is presented in Table 5.

TABLE 5

CLA yield in proportion to added linoleic acid amount

| Time (days) | Linoleic acid initially μg/ml | CLA (cis-9,tran-11) yield % |
|---|---|---|
| 3 | 600 | 95 |
| 4 | 1500 | 86 |

Example 7

Preparation of a Composition Containing Dried CLA

*Propionibacterium freudenreichii* ssp. *shermanii* JS was cultivated in a whey medium, which contained 2% whey permeate (Valio Oy), 0.5% casein hydrolysate (Valio Oy), 0.5% yeast extract (Lab M) and 0.2 g of linoleic acid micellized as in Example 1. The medium was inoculated with 1% of fresh bacterial culture, pH was maintained at 6.5 with an automatic pH adjustment unit and temperature was maintained at 30° C. during the cultivation. After four days of cultivation, the cell culture together with the medium was evaporated with a rotating evaporator to one fourth of the original and the obtained concentrate was freeze-dried in a Heto drier. The powder yield was 23 to 25 g/1000 ml. The obtained powder contained CLA 8.056 mg/g (193 mg/24 g powder), i.e. 96% of the original linoleic acid had been converted to ClA. Of the total CLA, 79% was the biologically most active isomer. The results are presented in Table 6.

TABLE 6

Production of CLA by PJS into growth medium

|  | PJS |
|---|---|
| Total amount CLA mg/g powder | 8.056 |
| c9,t11-isomer, mg/g | 6.373 |
| Linoleic acid, mg/g | 0.609 |

What is claimed is:

1. A method for preparing conjugated linoleic acid from linoleic acid by means of microorganisms, wherein the linoleic acid is added to a reaction broth in the form of micelles.

2. A method as claimed in claim 1, wherein the micelles also comprise a surfactant.

3. A method as claimed in claim 2, wherein the micelles are formed by reacting the free linoleic acid with the surfactant under alkaline conditions.

4. A method as claimed in claim 1, wherein the micelles comprise a mixture of linoleic acid and polyoxyethylene sorbitane mono-oleate.

5. A method as claimed in claim 1, wherein the conjugated linoleic acid prepared is mainly the cis-9,trans-11 isomer of conjugated linoleic acid.

6. A method as claimed in claim 1, wherein the conversion is performed with a propionic acid bacterium (bacteria).

7. A method as claimed in claim 6, wherein the propionic acid bacterium is a strain belonging to the species *Propionibacterium freudenreichii*.

8. A method as claimed in claim 7, wherein the propionic acid bacterium is *Propionibacterium freudenreichii* ssp. *freudenreichii* or *Propionibacterium freudenreichii* ssp. *shermanii*.

9. A method as claimed in claim 1, wherein the preparation of conjugated linoleic acid takes place simultaneously with the bacterial growth.

10. A method as claimed in claim 2, wherein the conversion is performed in the presence of the surfactant.

11. A method as claimed in claim 10, wherein the surfactant is polyoxyethylene sorbitane mono-oleate that is used in a concentration of 0.5 to 15%.

12. A method as claimed in claim 1, wherein the preparation of conjugated linoleic acid takes place after cultivation of bacteria.

13. A method as claimed in claim 12, wherein the conversion is performed with cells separated from the growth medium without a separate addition of surfactant.

14. A method as claimed in claim 1, wherein the preparation of conjugated linoleic acid takes place in connection with the preparation of a food product.

15. A method as claimed in claim 1, wherein the conjugated linoleic acid is isolated from the reaction broth and is optionally dried.

16. A method as claimed in claim 1, wherein the conjugated linoleic acid and the bacterial cells are concentrated and optionally dried.

17. A method as claimed in claim 16, wherein the conjugated linoleic acid and the bacterial cells are recovered, concentrated and lyophilized.

18. A method as claimed in claim 8, wherein the propionic acid bacterium is *Propionibacterium freudenreichii* ssp. *shermanii* JS DSM 7067.

* * * * *